(12) United States Patent
Sonnenberg et al.

(10) Patent No.: US 8,975,451 B2
(45) Date of Patent: Mar. 10, 2015

(54) SINGLE PHASE ESTER FEED FOR HYDROGENOLYSIS

(71) Applicant: Celanese International Corporation, Irving, TX (US)

(72) Inventors: Tatiana H. Sonnenberg, Houston, TX (US); Wei Qi, Houston, TX (US); R. Jay Warner, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/833,994

(22) Filed: Mar. 15, 2013

(65) Prior Publication Data

US 2014/0275640 A1 Sep. 18, 2014

(51) Int. Cl.
*C07C 27/04* (2006.01)
*C07C 29/149* (2006.01)

(52) U.S. Cl.
CPC .................................. *C07C 29/149* (2013.01)
USPC ........................................................ 568/884

(58) Field of Classification Search
CPC combination set(s) only.
See application file for complete search history.

(56) References Cited

U.S. PATENT DOCUMENTS

| | | |
|---|---|---|
| 1,469,447 A | 10/1923 | Schneible |
| 1,939,116 A | 12/1933 | Fuchs |
| 2,591,671 A | 4/1952 | Catterall |
| 2,591,672 A | 4/1952 | Catterall |
| 2,607,719 A | 8/1952 | Eliot et al. |
| 2,702,783 A | 2/1955 | Harrison et al. |
| 2,715,604 A | 8/1955 | Weaver, Jr. |
| 2,744,939 A | 5/1956 | Kennel |
| 2,801,209 A | 7/1957 | Muller et al. |
| 3,404,186 A | 10/1968 | Bailey et al. |
| 3,408,267 A | 10/1968 | Miller et al. |
| 3,445,345 A | 5/1969 | Katzen et al. |
| 3,884,981 A | 5/1975 | Kiff |
| 3,925,490 A | 12/1975 | Reich et al. |
| 3,990,952 A | 11/1976 | Katzen et al. |
| 4,262,154 A | 4/1981 | Gane et al. |
| 4,306,942 A | 12/1981 | Brush et al. |
| 4,328,375 A | 5/1982 | Barlow |
| 4,338,221 A | 7/1982 | Qualeatti |
| 4,352,947 A | 10/1982 | Habib et al. |
| 4,370,491 A | 1/1983 | Bott et al. |
| 4,379,028 A | 4/1983 | Berg et al. |

(Continued)

FOREIGN PATENT DOCUMENTS

| | | |
|---|---|---|
| CA | 1233484 | 3/1988 |
| CN | 201768393 | 3/2011 |

(Continued)

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(Continued)

*Primary Examiner* — Karl J Puttlitz (57) ABSTRACT

The process involves esterifying ethanol and acetic acid to produce an esterification product that is in a single phase that is directly reduced, by hydrogenolysis, to produce ethanol. The single phase is not capable of separating. Feeding a single phase feed stream reduces the separation of the esterification product. Hydrogen may be fed to the esterification reactor that operates at a high pressure that is substantially similar to or greater than the hydrogenolysis reactor.

9 Claims, 2 Drawing Sheets

(56) References Cited

U.S. PATENT DOCUMENTS

| | | |
|---|---|---|
| 4,395,576 A | 7/1983 | Kwantes et al. |
| 4,398,039 A | 8/1983 | Pesa et al. |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,448,644 A | 5/1984 | Foster et al. |
| 4,454,358 A | 6/1984 | Kummer et al. |
| 4,456,775 A | 6/1984 | Travers et al. |
| 4,476,326 A | 10/1984 | Lin et al. |
| 4,481,146 A | 11/1984 | Leupold et al. |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster et al. |
| 4,541,897 A | 9/1985 | Sommer et al. |
| 4,600,571 A | 7/1986 | McCarroll et al. |
| 4,611,085 A | 9/1986 | Kitson |
| 4,628,130 A | 12/1986 | Bournonville et al. |
| 4,678,543 A | 7/1987 | Houben et al. |
| 4,751,334 A | 6/1988 | Turner et al. |
| 4,758,600 A | 7/1988 | Arimitsu et al. |
| 4,761,505 A | 8/1988 | Diana et al. |
| 4,774,365 A | 9/1988 | Chen et al. |
| 4,837,367 A | 6/1989 | Gustafson et al. |
| 4,837,368 A | 6/1989 | Gustafson et al. |
| 4,842,693 A | 6/1989 | Wheldon |
| 4,943,354 A | 7/1990 | Osterburg et al. |
| 4,985,572 A | 1/1991 | Kitson et al. |
| 5,004,845 A | 4/1991 | Bradley et al. |
| 5,035,776 A | 7/1991 | Knapp |
| 5,047,592 A | 9/1991 | Carpenter |
| 5,061,671 A | 10/1991 | Kitson et al. |
| 5,124,004 A | 6/1992 | Grethlein et al. |
| 5,149,680 A | 9/1992 | Kitson et al. |
| 5,185,476 A | 2/1993 | Gustafson |
| 5,185,481 A | 2/1993 | Muto et al. |
| 5,196,601 A | 3/1993 | Kitsuki et al. |
| 5,198,592 A | 3/1993 | van Beijnum et al. |
| 5,215,902 A | 6/1993 | Tedder |
| 5,220,020 A | 6/1993 | Buchwald et al. |
| 5,250,271 A | 10/1993 | Horizoe et al. |
| 5,284,983 A | 2/1994 | Muto et al. |
| 5,334,751 A | 8/1994 | Lemanski et al. |
| 5,403,962 A | 4/1995 | Schneider et al. |
| 5,414,161 A | 5/1995 | Uhm et al. |
| 5,426,246 A | 6/1995 | Nagahara et al. |
| 5,449,440 A | 9/1995 | Rescalli et al. |
| 5,476,974 A | 12/1995 | Moore et al. |
| 5,480,665 A | 1/1996 | Smith |
| 5,488,185 A | 1/1996 | Ramachandran et al. |
| 5,502,094 A | 3/1996 | Moore et al. |
| 5,502,248 A | 3/1996 | Funk et al. |
| 5,565,068 A | 10/1996 | Parker et al. |
| 5,567,765 A | 10/1996 | Moore et al. |
| 5,658,962 A | 8/1997 | Moore et al. |
| 5,747,486 A | 5/1998 | Sohda et al. |
| 5,770,761 A | 6/1998 | Lin et al. |
| 5,831,133 A | 11/1998 | Mimoun |
| 5,993,610 A | 11/1999 | Berg |
| 5,998,658 A | 12/1999 | Wu et al. |
| 6,024,176 A | 2/2000 | Moore et al. |
| 6,046,127 A | 4/2000 | Mimoun |
| 6,093,845 A | 7/2000 | van Acker et al. |
| 6,121,497 A | 9/2000 | Murphy |
| 6,204,299 B1 | 3/2001 | Moore et al. |
| 6,214,253 B1 | 4/2001 | Moore et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,572 B1 | 10/2002 | Zhou et al. |
| 6,486,368 B1 | 11/2002 | Zhou et al. |
| 6,491,983 B2 | 12/2002 | Moore et al. |
| 6,509,180 B1 | 1/2003 | Verser et al. |
| 6,525,230 B2 | 2/2003 | Grosso |
| 6,552,220 B1 | 4/2003 | Obana et al. |
| 6,632,330 B1 | 10/2003 | Colley et al. |
| 6,693,213 B1 | 2/2004 | Kolena et al. |
| 6,713,655 B2 | 3/2004 | Yilmaz et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,863,211 B2 | 3/2005 | Moore et al. |
| 6,867,164 B2 | 3/2005 | Obana et al. |
| 6,927,048 B2 | 8/2005 | Verser et al. |
| 7,019,182 B2 | 3/2006 | Grosso |
| 7,074,603 B2 | 7/2006 | Verser et al. |
| 7,091,155 B2 | 8/2006 | Inui et al. |
| 7,148,390 B2 | 12/2006 | Zhou et al. |
| 7,161,050 B2 | 1/2007 | Sherman et al. |
| 7,230,150 B2 | 6/2007 | Grosso et al. |
| 7,351,559 B2 | 4/2008 | Verser et al. |
| 7,361,794 B2 | 4/2008 | Grosso |
| 7,507,562 B2 | 3/2009 | Verser et al. |
| 7,553,397 B1 | 6/2009 | Colley et al. |
| 7,572,353 B1 | 8/2009 | Vander et al. |
| 7,594,981 B2 | 9/2009 | Ikeda |
| 7,608,744 B1 | 10/2009 | Johnston et al. |
| 7,652,167 B2 | 1/2010 | Miller et al. |
| 7,667,068 B2 | 2/2010 | Miller et al. |
| 7,682,812 B2 | 3/2010 | Verser et al. |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,838,708 B2 | 11/2010 | Sherman et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 7,964,379 B2 | 6/2011 | Verser et al. |
| 8,002,953 B2 | 8/2011 | Lee et al. |
| 8,053,610 B2 | 11/2011 | Kikuchi et al. |
| 8,062,482 B2 | 11/2011 | Warner |
| 8,080,684 B2 | 12/2011 | Hassan et al. |
| 8,088,832 B2 | 1/2012 | Melnichuk et al. |
| 8,129,436 B2 | 3/2012 | Tirtowidjojo et al. |
| 8,198,057 B2 | 6/2012 | Padgett |
| 8,288,596 B2 | 10/2012 | Garton et al. |
| 8,299,132 B2 | 10/2012 | Gracey et al. |
| 8,299,133 B2 | 10/2012 | Gracey et al. |
| 8,378,153 B2 | 2/2013 | Daniel et al. |
| 8,502,001 B2 | 8/2013 | Daniel et al. |
| 8,524,954 B2 | 9/2013 | Ditzel et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0063184 A1 | 4/2004 | Grichko |
| 2004/0152915 A1 | 8/2004 | Fujita et al. |
| 2004/0195084 A1 | 10/2004 | Hetherington et al. |
| 2004/0242917 A1 | 12/2004 | Inui et al. |
| 2005/0043572 A1 | 2/2005 | Grosso |
| 2005/0192468 A1 | 9/2005 | Sherman et al. |
| 2005/0214408 A1 | 9/2005 | Pilkington et al. |
| 2006/0019360 A1 | 1/2006 | Verser et al. |
| 2006/0127999 A1 | 6/2006 | Verser et al. |
| 2006/0224013 A1 | 10/2006 | Inui et al. |

(56) References Cited

U.S. PATENT DOCUMENTS

| | | | |
|---|---|---|---|
| 2006/0252956 A1 | 11/2006 | Miller et al. | |
| 2007/0144886 A1 | 6/2007 | Sylvester et al. | |
| 2007/0265360 A1 | 11/2007 | Luo et al. | |
| 2008/0135396 A1 | 6/2008 | Blum | |
| 2009/0005588 A1 | 1/2009 | Hassan et al. | |
| 2009/0023192 A1 | 1/2009 | Verser et al. | |
| 2009/0081749 A1 | 3/2009 | Verser et al. | |
| 2009/0166172 A1 | 7/2009 | Casey et al. | |
| 2009/0264285 A1 | 10/2009 | Luo et al. | |
| 2010/0030002 A1 | 2/2010 | Johnston et al. | |
| 2010/0069515 A1 | 3/2010 | Tirtowidjojo et al. | |
| 2010/0080736 A1 | 4/2010 | Hassan et al. | |
| 2010/0121119 A1 | 5/2010 | Sherman et al. | |
| 2010/0185021 A1 | 7/2010 | Ross et al. | |
| 2010/0261800 A1 | 10/2010 | Daniel et al. | |
| 2010/0273229 A1 | 10/2010 | Verser et al. | |
| 2010/0311138 A1 | 12/2010 | Padgett | |
| 2011/0004034 A1 | 1/2011 | Daniel et al. | |
| 2011/0034741 A1 | 2/2011 | Sherman et al. | |
| 2011/0046421 A1 | 2/2011 | Daniel et al. | |
| 2011/0224462 A1 | 9/2011 | Ditzel et al. | |
| 2013/0131198 A1 | 5/2013 | Warner et al. | |
| 2013/0131393 A1 | 5/2013 | Warner et al. | |
| 2013/0131394 A1* | 5/2013 | Warner et al. | 568/884 |
| 2013/0131395 A1* | 5/2013 | Warner et al. | 568/884 |
| 2013/0131396 A1* | 5/2013 | Warner et al. | 568/885 |
| 2013/0131397 A1 | 5/2013 | Warner et al. | |
| 2013/0131398 A1* | 5/2013 | Warner et al. | 568/885 |
| 2013/0131400 A1 | 5/2013 | Duff et al. | |
| 2013/0158297 A1* | 6/2013 | Johnson et al. | 568/876 |
| 2013/0158302 A1 | 6/2013 | Duff et al. | |
| 2014/0039225 A1 | 2/2014 | Daniel et al. | |
| 2014/0163263 A1* | 6/2014 | Wollrab et al. | 568/885 |

FOREIGN PATENT DOCUMENTS

| | | |
|---|---|---|
| CN | 102091429 | 6/2011 |
| CN | 101525272 | 5/2012 |
| CN | 202214306 | 5/2012 |
| DE | 2723611 | 11/1973 |
| EP | 0104197 | 4/1984 |
| EP | 0137749 | 4/1985 |
| EP | 0944572 | 4/2002 |
| EP | 2060553 | 5/2009 |
| JP | 2-215790 | 8/1990 |
| JP | 5186391 | 7/1993 |
| JP | 6-009454 | 1/1994 |
| JP | 6-025033 | 2/1994 |
| JP | 6-128181 | 5/1994 |
| JP | 2009-106274 | 5/2009 |
| JP | 2009-263356 | 11/2009 |
| JP | 2010-159212 | 7/2010 |
| WO | WO 82/03854 | 11/1982 |
| WO | WO 83/03409 | 10/1983 |
| WO | WO 98/25876 | 6/1998 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |

OTHER PUBLICATIONS

Zhang, et al., Hydrogenation of Ethyl Acetate to Ethanol over Ni-Based Catalysts Obtained from Ni/Al Hydrotalcite-Like Compounds. Molecules 2010, 15, 5139-5152, 2010.

Subramani et al., "A Review of Recent Literature to Search for an Efficient Catalytic Process for the Conversion of Syngas to Ethanol," Energy & Fuels, 2008, vol. 22, pp. 814-839.

Juran et al., "Convert Methanol to Ethanol", Hydrocarbon Processing, Oct. 1985, pp. 85-87.

\* cited by examiner

SINGLE PHASE ESTER FEED FOR HYDROGENOLYSIS

FIELD OF THE INVENTION

The present invention relates generally to alcohol production from an esterification product that withdrawn as a single phase ester feed, and in particular to producing ethanol through reducing the single phase ester feed.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds, including esters, has been widely studied, and a variety of combinations of catalysts, supports, and operating conditions have been mentioned in the literature. Copper-iron catalysts for hydrogenolyzing esters to alcohols are described in U.S. Pat. No. 5,198,592. A hydrogenolysis catalyst comprising nickel, tin, germanium and/or lead is described in U.S. Pat. No. 4,628,130. A rhodium hydrogenolysis catalyst that also contains tin, germanium and/or lead is described in U.S. Pat. No. 4,456,775.

Several processes that produce ethanol from acetates, including methyl acetate and ethyl acetate, are known in the literature.

WO8303409 describes producing ethanol by carbonylation of methanol by reaction with carbon monoxide in the presence of a carbonylation catalyst to form acetic acid which is then converted to an acetate ester followed by hydrogenolysis of the acetate ester formed to give ethanol or a mixture of ethanol and another alcohol which can be separated by distillation. Preferably the other alcohol or part of the ethanol recovered from the hydrogenolysis step is recycled for further esterification. Carbonylation can be effected using a $CO/H_2$ mixture and hydrogenolysis can similarly be conducted in the presence of carbon monoxide, leading to the possibility of circulating gas between the carbonylation and hydrogenolysis zones with synthesis gas, preferably a 2:1 $H_2$:CO molar mixture being used as makeup gas.

WO2009063174 describes a continuous process for the production of ethanol from a carbonaceous feedstock. The carbonaceous feedstock is first converted to synthesis gas which is then converted to ethanoic acid, which is then esterified and which is then hydrogenated to produce ethanol.

WO2009009320 describes an indirect route for producing ethanol. Carbohydrates are fermented under homoacidogenic conditions to form acetic acid. The acetic acid is esterified with a primary alcohol having at least 4 carbon atoms and hydrogenating the ester to form ethanol.

US Pub. No. 20110046421 describes a process for producing ethanol comprising converting carbonaceous feedstock to syngas and converting the syngas to methanol. Methanol is carbonylated to ethanoic acid, which is then subjected to a two stage hydrogenation process. First the ethanoic acid is converted to ethyl ethanoate followed by a secondary hydrogenation to ethanol.

US Pub. No. 20100273229 describes a process for producing acetic acid intermediate from carbohydrates, such as corn, using enzymatic milling and fermentation steps. The acetic acid intermediate is acidified with calcium carbonate and the acetic acid is esterified to produce esters. Ethanol is produced by a hydrogenolysis reaction of the ester.

U.S. Pat. No. 5,414,161 describes a process for producing ethanol by a gas phase carbonylation of methanol with carbon monoxide followed by a hydrogenation. The carbonylation produces acetic acid and methyl acetate, which are separated and the methyl acetate is hydrogenated to produce ethanol in the presence of a copper-containing catalyst.

U.S. Pat. No. 4,497,967 describes a process for producing ethanol from methanol by first esterifying the methanol with acetic acid. The methyl acetate is carbonylated to produce acetic anhydride which is then reacted with one or more aliphatic alcohols to produce acetates. The acetates are hydrogenated to produce ethanol. The one or more aliphatic alcohols formed during hydrogenation are returned to the acetic anhydride esterification reaction.

U.S. Pat. No. 4,454,358 describes a process for producing ethanol from methanol. Methanol is carbonylated to produce methyl acetate and acetic acid. The methyl acetate is recovered and hydrogenated to produce methanol and ethanol. Ethanol is recovered by separating the methanol/ethanol mixture. The separated methanol is returned to the carbonylation process.

The need remains for improved processes for efficient ethanol production by reducing esters on a commercially feasible scale.

SUMMARY OF THE INVENTION

In a first embodiment, the present invention is directed to a method of producing ethanol comprising esterifying acetic acid and ethanol in a first reaction zone to produce an effluent that is not capable of phasing, and preferably the effluent comprises at least 20 wt. % ethanol; adding hydrogen to the effluent to form a feed stream that may comprise from 70 mol. % to 95 mol. % hydrogen; reacting the feed stream in a second reaction zone under conditions to reduce ethyl acetate to ethanol to produce a crude reactor product; and recovering ethanol from the crude reactor product. In one embodiment, the acetic acid and ethanol molar ratio in the first reaction zone is from 1:3 to 1:10, and the first reaction zone is operated in the vapor phase. The crude reactor product produced by the second reaction zone may comprise more ethanol than the effluent on a weight basis, and may preferably contain 70 to 97 wt. % ethanol, 1 to 15 wt. % ethyl acetate, and 1 to 15 wt. % water. The second reaction zone may operate at a pressure that is from 700 kPa to 8,500 kPa.

In a second embodiment, the present invention is directed to a method of producing ethanol comprising esterifying acetic acid and ethanol in a first reaction zone to produce an effluent that is not capable of phasing; reacting effluent and hydrogen in a second reaction zone under conditions to reduce ethyl acetate to ethanol to produce a crude reactor product; flashing the crude reactor product to obtain a hydrogen stream and a liquid stream; returning the hydrogen stream to the second reaction zone; and recovering ethanol from the liquid stream. A portion of the ethanol recovered from the liquid may be returned to the first reaction zone.

In a third embodiment, the present invention is directed to a method of producing ethanol comprising esterifying acetic acid and ethanol in a first reaction zone to produce an effluent that is not capable of phasing; reacting effluent and hydrogen in a second reaction zone under conditions to reduce ethyl acetate to ethanol to produce a crude reactor product, and separating at least a portion of the crude reactor product, preferably a liquid portion thereof, in a distillation column. In one embodiment, the process may comprise withdrawing an overhead comprising ethyl acetate; and introducing the overhead to the second reaction zone. In another embodiment, ethanol may be withdrawn as sidedraw from the distillation column and the process may further comprise dehydrating the sidedraw to obtain an ethanol product having less than 0.5 wt. % water.

In a fourth embodiment, the present invention is directed to a method of producing ethanol comprising introducing acetic acid, ethanol, and hydrogen to a first reaction zone operating at a pressure from 700 kPa to 2,900 kPa and under conditions to esterify the acetic acid and ethanol to produce a feed stream, reacting the feed stream in a second reaction zone under conditions, and preferably at a pressure that is from 700 kPa to 2,900 kPa, to reduce ethyl acetate to ethanol and produce a crude reactor product; and recovering ethanol from the crude reactor product. In one embodiment, the operating pressure of the first reaction zone is substantially similar or greater than the operating pressure of the second reaction zone. For purposes of the present invention, substantially similar refers to an operating pressure that varies by less than 10% between the first and second reaction zones. The feed stream may comprise from 70 mol. % to 95 mol. % hydrogen. In one embodiment, all of the hydrogen fed to the second reaction zone passes through the first reaction zone.

In a fifth embodiment, the present invention is directed to a method of producing ethanol comprising introducing acetic acid, ethanol, and hydrogen to a first reaction zone under conditions to esterify the acetic acid and ethanol to produce a feed stream, reacting the feed stream in a second reaction zone under conditions to reduce ethyl acetate to ethanol and produce a crude reactor product, wherein the first reaction zone is operating at a pressure that is substantially similar or greater than an operating pressure of the second reaction zone; and recovering ethanol from the crude reactor product.

In a sixth embodiment, the present invention is directed to a method of producing ethanol comprising introducing acetic acid, ethanol, and hydrogen to a first reaction zone under conditions to esterify the acetic acid and ethanol to produce a feed stream comprising from 70 mol. % to 95 mol. % hydrogen, reacting the feed stream in a second reaction zone under conditions to reduce ethyl acetate to ethanol and produce a crude reactor product, wherein all of the hydrogen fed to the second reaction zone passes through the first reaction zone; and recovering ethanol from the crude reactor product.

In a seventh embodiment, the present invention is directed to a method of producing ethanol comprising introducing acetic acid, ethanol, and hydrogen to a first reaction zone under conditions to esterify the acetic acid and ethanol to produce a feed stream, reacting the feed stream in a second reaction zone under conditions to reduce ethyl acetate to ethanol and produce a crude reactor product; flashing the crude reactor product to obtain a hydrogen stream and a liquid stream; returning the hydrogen stream to the first reaction zone; and recovering ethanol from the liquid stream. In one embodiment, the first reaction zone may be operating at a pressure that is substantially similar or greater than the second reaction zone. The operating pressure of the first reaction zone may be from 700 kPa to 2,900 kPa.

In an eighth embodiment, the present invention is directed to a method of producing ethanol comprising introducing acetic acid, ethanol, and hydrogen to a first reaction zone under conditions to esterify the acetic acid and ethanol to produce a feed stream, reacting the feed stream in a second reaction zone under conditions to reduce ethyl acetate to ethanol and produce a crude reactor product; and separating at least a portion of the crude reactor product, preferably a liquid portion thereof, in a distillation column. In one embodiment, the process may comprise withdrawing an overhead comprising ethyl acetate; and introducing the overhead to the second reaction zone. In another embodiment, ethanol may be withdrawn as sidedraw from the distillation column and the process may further comprise dehydrating the sidedraw to obtain an ethanol product having less than 0.5 wt. % water.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to processes for producing ethanol from acetic acid through an acetate intermediate. In particular, the process involves esterifying ethanol and acetic acid to produce an esterification product that is in a single phase that is directly reduced, by hydrogenolysis, to produce ethanol. The esterification may be conducted in the liquid or vapor phase, but vapor phase is preferable to achieve higher conversions of acetic acid and to provide a vapor effluent of the esterification reactor may be fed to the hydrogenolysis reactor. For purposes of the present invention, a single phase esterification product refers to a composition comprising ethyl acetate, ethanol, and water that is not capable of phasing into an aqueous phase or organic phase. When the esterification product is in the vapor phase, the single phase is not capable of phasing when condensed. In one embodiment, the single phase esterification product may comprise hydrogen. Because the esterification product is not capable of phasing and remains as a single phase the esterification product does not need further purification prior to producing ethanol. This provides an advantage to reduce the separation and purification of the esterification product prior to hydrogenolysis.

In one embodiment, a single phase esterification product may comprise from 20 to 60 wt. % ethyl acetate, from 20 to 70 wt. % ethanol, from 1 to 30 wt. % water, and from 0 to 15 wt. % acetic acid. In a preferred embodiment, a single phase esterification product may comprise from 25 to 55 wt. % ethyl acetate, from 30 to 65 wt. % ethanol, from 2 to 25 wt. % water, and from 0.01 to 10 wt. % acetic acid. To prevent phasing the ethanol concentration is preferably at least 20 wt. %, e.g., at least 25 wt. % or at least 30 wt. %. Lower acetic acid concentrations are preferred. Acetic acid should preferably be kept in low concentrations in the single phase esterification product to avoid problems with the catalyst used for the reduction step. Hydrogen may be added separately after the esterification and does not cause the esterification product to phase. In one embodiment, the molar ratio of water to hydrogen in the feed stream after hydrogen is added is from 1:5 to 1:25, e.g., from 1:10 to 1:20.

In some embodiments, when hydrogen is fed to a high pressure esterification reactor, the single phase esterification product may also comprise hydrogen in an amount from 70 mol. % to 95 mol. %, e.g., 80 mol. % to 92 mol. %. The addition of hydrogen has little impact on the phasing of the esterification product and preferably does not cause the esterification product to phase. When hydrogen is present, the remaining components of the single phase esterification product may comprise from 10 to 50 wt. % ethyl acetate, from 15 to 60 wt. % ethanol, from 0.5 to 25 wt. % water, from 0 to 10 wt. % acetic acid, and the balancing being hydrogen in an amount up to 30 wt. %, e.g. up to 25 wt. % or up to 20 wt. %.

The present invention provides an advantageous method of producing an ester feed from the esterification product so that the ester feed is suitable for hydrogenolysis. Pure ethyl acetate may be less cost effective in producing ethanol than acetic acid, and to provide a cost effective ester feed embodiments of the present invention simplify the esterification system by eliminating ethyl acetate separation. In addition, the present invention provides efficient separation processes for recovering ethanol after the hydrogenolysis of ethyl acetate. The processes of the present invention advantageously provide commercially feasible scale for producing ethanol.

Controlling the molar ratio of acetic acid to ethanol in the esterification provides an esterification product that is not capable of phasing. The present invention preferably uses an excess of ethanol. An excess of ethanol reduces the amount of unreacted acetic acid in the reactor effluent from the esterification process. Advantageously, this allows the esterification product to be directly fed to the hydrogenolysis reactor without further removing acetic acid. In addition, excess ethanol increases the ethanol concentration in the reactor effluent so that it remains in a single phase. In one embodiment, the molar ratio of acetic acid to ethanol fed to the esterification reactor may be from 1:3 to 1:10, e.g., from 1:4 to 1:8.

In conventional ester production processes, especially in the liquid phase, it is necessary to add ethyl acetate to maintain an azeotrope in the top of the reactive distillation column as described in U.S. Pat. No. 6,768,021. The present invention does not have separation in the esterification process and the reactor effluent is withdrawn in a single phase. Thus, the present invention eliminates the need to recycle ethyl acetate to the esterification process to maintain the azeotrope.

Reactant Sources

The present invention comprises producing ethanol from acetic acid by esterifying the acetic acid to form an ester and reducing the ester to an alcohol. The embodiments of the present invention may also be integrated with methods for producing acetic acid and/or methods for producing ethanol. For example, acetic acid may be produced from methanol, and thus ethanol production according to embodiments of the present invention may be produced from methanol. In one embodiment, the present invention comprises producing ethanol from methanol by carbonylating the methanol to form acetic acid, esterifying the acetic acid to form an ester in a single phase esterification product, and reducing the ester to form ethanol. In yet another embodiment, the present invention comprises producing methanol from syngas, carbonylating the methanol to form acetic acid, esterifying the acetic acid to form an ester in a single phase esterification product, and reducing the ester to an alcohol, namely ethanol. In still another embodiment, the present invention comprises producing ethanol from a carbon source, such as coal, biomass, petroleum, or natural gas, by converting the carbon source to syngas, followed by converting the syngas to methanol, carbonylating the methanol to form acetic acid, esterifying the acetic acid to form an ester in a single phase esterification product, and reducing the ester to an alcohol. In still another embodiment, the present invention comprises producing ethanol from a carbon source, such as coal, biomass, petroleum, or natural gas, by converting the carbon source to syngas, separating the syngas into a hydrogen stream and a carbon monoxide stream, carbonylating a methanol with the carbon monoxide stream to form acetic acid, esterifying the acetic acid to form an ester in a single phase esterification product, and reducing the ester to an alcohol. In addition, the ester may be reduced with the hydrogen stream. Also, methanol may be produced from the syngas.

The esterification reactants, acids and alcohols, used in connection with the process of this invention may be derived from any suitable source including carbon source such as natural gas, petroleum, coal, biomass, and so forth. Acetic acid may be produced by several methods, including but not limited to, methanol carbonylation, acetaldehyde oxidation, ethane/ethylene oxidation, oxidative fermentation, and anaerobic fermentation.

In one embodiment, the production of ethanol may be integrated with such methanol carbonylation processes. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. A carbonylation system preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volumes*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^{-H+}$, $[Ir(CH_3)I_3(CO_2)]^-H^+$, $Ir_4(CO)_{12}$, $IrCl_3 \cdot 3H_2O$, $IrBr_3 \cdot 3H_2O$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 wppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

A halogen co-catalyst/promoter is generally used in combination with the Group VIII metal catalyst component. Methyl iodide is a preferred halogen promoter. Preferably, the concentration of the halogen promoter in the reaction medium ranges from 1 wt. % to 50 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1. A suitable promoter concentration is 400 to 5000 wppm.

The temperature of the carbonylation reaction in the reactor may be from 150° C. to 250° C. and a pressure from 1 to 20 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Water may be formed in situ in the reaction medium, for example, by the esterification reaction between methanol reactant and acetic acid product. In some embodiments, water is introduced to the reactor together with or separately from the other components of the reaction medium. Water may be separated from the other components of the reaction product withdrawn from reactor and may be recycled in controlled amounts to maintain the required concentration of water in the reaction medium. The concentration of water maintained in the reaction medium ranges from 0.1 wt. % to 16 wt. % of the total weight of the reaction product.

The desired reaction rates are obtained even at low water concentrations by maintaining in the reaction medium a concentration of methyl acetate, and an additional iodide ion that is over and above the iodide ion that is present as hydrogen iodide. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present together. The absolute concentration of iodide ion is not a limitation on the usefulness of the present invention. In low water carbonylation, the additional iodide over and above the organic iodide promoter may be present in the catalyst solution in amounts ranging from 2 wt. % to 20 wt. %; the methyl acetate may be present in amounts ranging from 0.5 wt. % to 30 wt. %; and the lithium iodide may be present in amounts ranging from 5 wt. % to 20 wt. %. The catalyst may be present in the catalyst solution in amounts ranging from 200 wppm to 2000 wppm.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the esterification reaction zone of the present invention without the need for condensing the acetic acid and light ends or removing water, saving overall processing costs.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenolysis step may be supplied from syngas.

In some embodiments, some or all of the raw materials may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the ethyl acetate to form the crude reaction product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the esterification may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenolysis step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Biomass-derived syngas has a detectable $^{14}C$ isotope content as compared to fossil fuels such as coal or natural gas. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid feed stream that is fed to the esterification step may also comprise other carboxylic acids and anhydrides, acetaldehyde, and acetone. In one aspect, the acetic acid feed stream comprises one or more of the compounds selected from the group consisting of acetic acid, propionic acid, acetic anhydride, acetaldehyde, ethyl acetate, diethyl acetal, and mixtures thereof. These other compounds may also be hydrogenated in the processes of the present invention. Water may also be present, generally in amounts of less than 10 wt. %, in the acetic acid feed.

The alcohol feed stream fed to the esterification step may comprise methanol, ethanol, and/or butanol. In one aspect, the feed stream primarily comprises ethanol. Ethanol may be obtained from a widely used bio-fermentation process and/or wood pyrolysis. Ethanol may also be produced by hydrating ethylene. In some embodiments, ethanol may be obtained by reducing acetic acid with hydrogen to ethanol in the presence of a Co catalyst or a Pt—Sn catalyst, as described in U.S. Pat. Nos. 7,863,489, and 7,608,744, the entire contents of which are hereby incorporated by reference. In addition, as described herein, a portion of the ethanol may be obtained from the products of the hydrogenolysis reactor.

In one embodiment, the ethanol feed stream may also comprise minor amounts of $C_1$ to $C_4$ alcohols, aldehydes, acetals, hemiacetals, ethers and mixtures thereof. In one embodiment, the ethanol feed stream may comprise low concentrations of water, e.g., less than 10 wt. % or less than 5 wt. %.

Esterification Reaction

Figure 1:
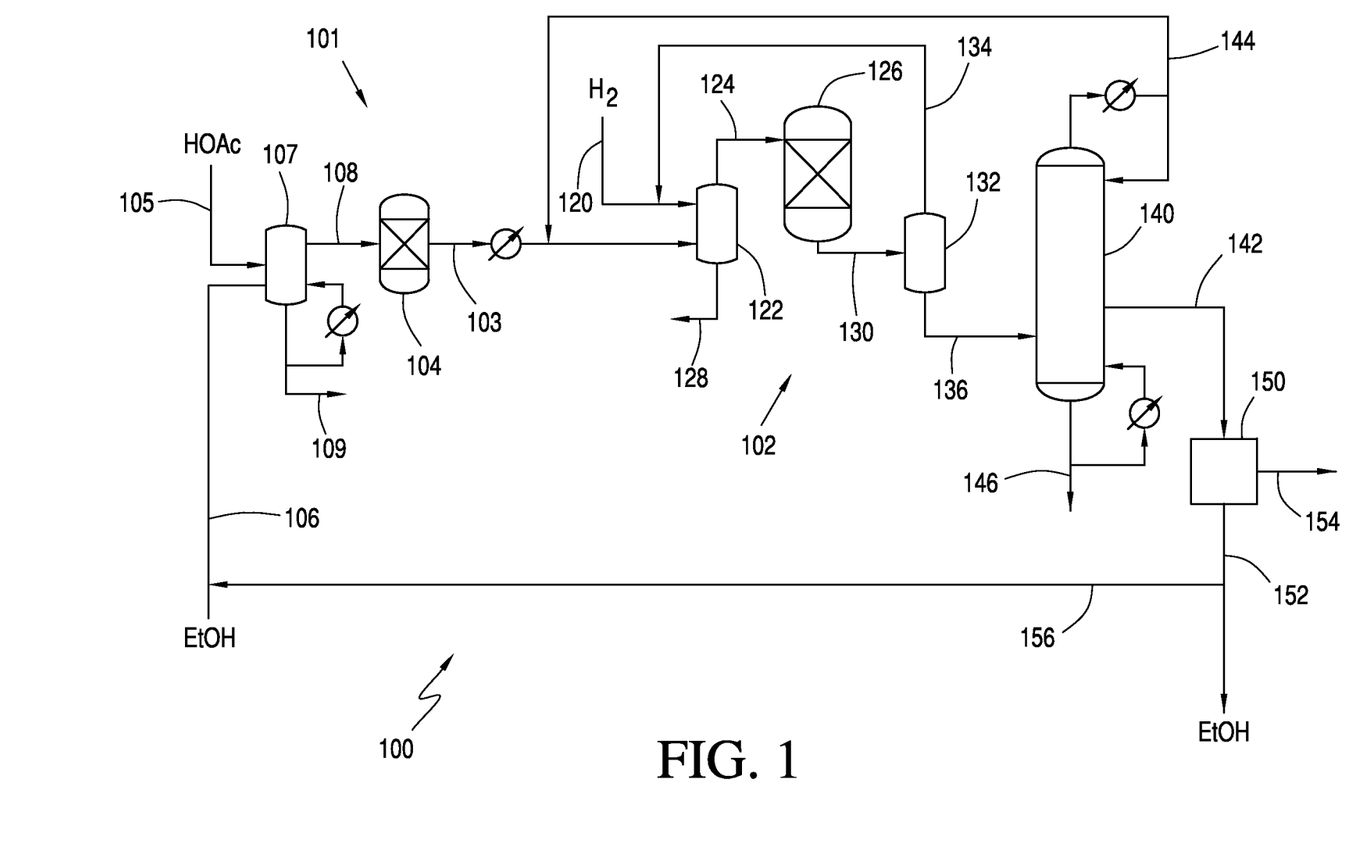
FIG. 1 is a schematic diagram of ethanol production process that directly feeds a single phase esterification product produced by vapor esterification to the hydrogenolysis zone in accordance with one embodiment of the present invention.

The process 100 of the present invention comprises an esterification zone 101 and a hydrogenolysis zone 102 as shown in FIG. 1. The process may be operated continuously or batchwise. Esterification may be carried out in either the liquid or vapor phase. Liquid phase esterification of acetic acid and ethanol has an equilibrium constant, $K_x$, of about 4, while vapor phase esterification of acetic acid and ethanol has a higher equilibrium constant, $K_x$, of about 30 at 130° C. Vapor phase esterification is preferred so that the reactor effluent 103 is in the vapor phase and may be directly fed to hydrogenolysis zone 102. As stated above, an excess molar ratio of ethanol is fed to the esterification reactor so that the conversion of acetic acid is high, e.g., greater than 90%, or more preferably greater than 99%.

Figure 2:
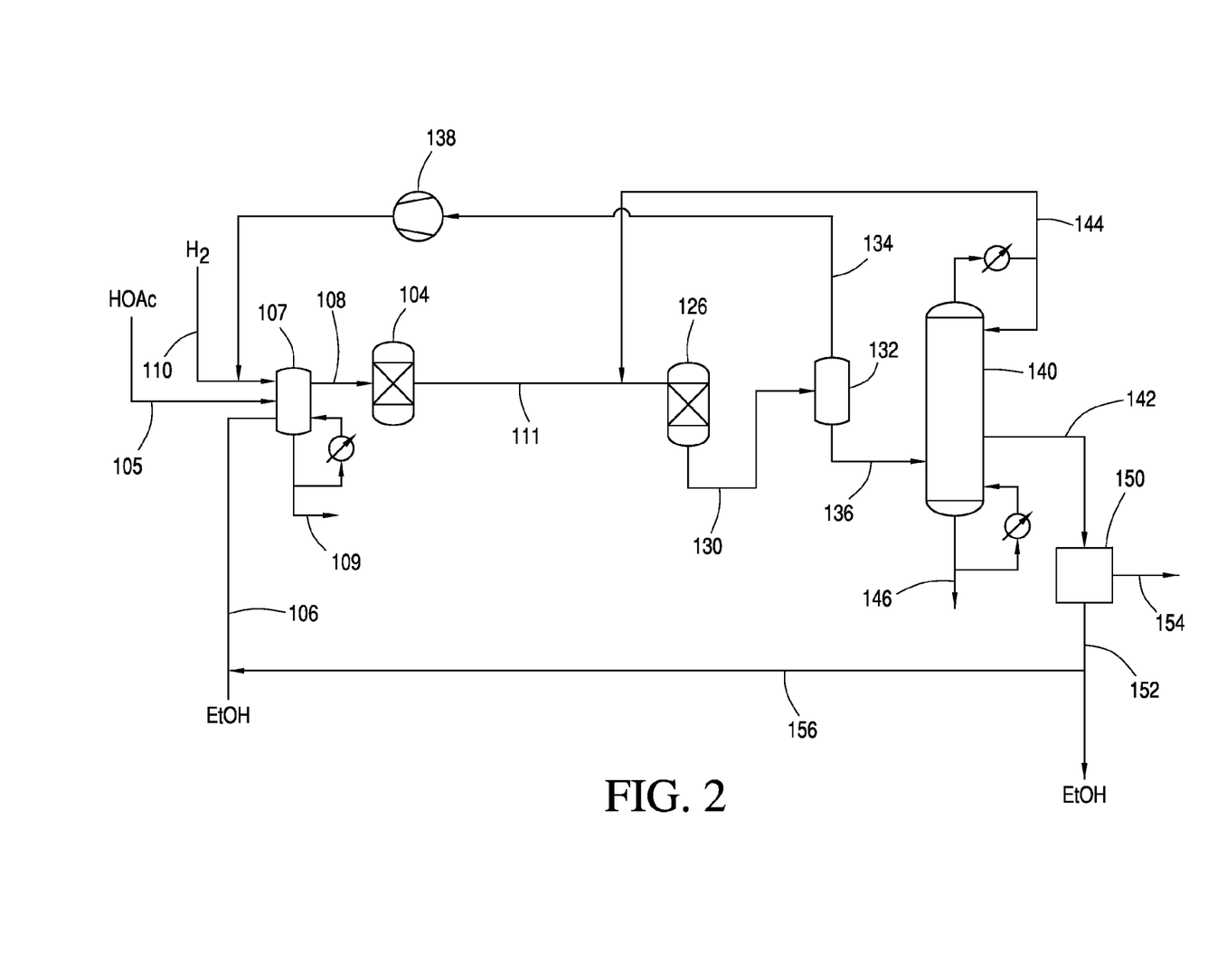
FIG. 2 is a schematic diagram of ethanol production process that directly feeds a single phase esterification product with hydrogen produced by vapor esterification operated at high pressures to the hydrogenolysis zone in accordance with one embodiment of the present invention.

The formation of the esterification product in the esterification equilibrium reaction may be enhanced by the presence of a catalyst. A variety of homogeneous or heterogeneous acid catalysts may also be employed within the scope of this invention. The catalyst should be stable at the desired reaction temperature. Suitable catalysts include, without limitation, sulfuric acid, sulfonic acid, alkyl sulfonic acids, and aromatic sulfonic acids. Alkyl sulfonic and aromatic sulfonic acids may include methane sulfonic acid, benzene sulfonic acid and p-toluene sulfonic acid. In one embodiment, an ion exchange resin, e.g., Amberlyst™ 15, Amberlyst™ 36, Amberlyst™ 70, or Purolite™ CT179, may be used. Sulfuric acid, acidic zeolites, or heteropoly acids can also be used within the scope of the invention. When hydrogen is also fed to the esterification process, under high pressure as shown in FIG. 2, the esterification catalyst should be selected to avoid promoting hydrogenation reactions.

Vapor phase esterification may be carried out in a reactor 104. Due to the single phase esterification product there is no need for additional purification or separation in the esterification zone 101. Suitable reactors, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween. Reactor 104 may be a fixed-bed reactor and may comprise a heterogeneous catalyst.

In another embodiment, the reaction may be carried out in the vapor phase using a heterogeneous reactive distillation column.

Acetic acid feed stream in line 105 and ethanol feed stream in line 106, respectively, are fed to a vaporizer 107 to create a vapor feed stream in line 108 that is directed to reactor 104. In one embodiment, prior to feeding into vaporizer 107, the acetic acid feed stream and/or ethanol feed stream may be preheated. Vaporizer 107 may be fed with liquid reactants or vapor reactants, and preferably all the reactants are in the liquid phase. The acetic acid and ethanol may be vaporized at or near the reaction temperature. For reactions conducted in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature.

As shown in FIG. 1, acetic acid feed stream in line 105 may be fed to the top of vaporizer 107 and ethanol feed stream in line 106 may be fed at a point below the acetic acid feed stream point. The location of the feed points to vaporizer 107 may vary depending on the vessel configuration. Vaporizer 107 may be a vessel equipped with heat energy input sufficient to vaporize the liquid feed. The vessel may be jacketed, contain internal heating coils, or contain external thermosyphon, or forced circulation type reboilers. Optionally, lines 105 and 106 may be combined and jointly fed to vaporizer 107. Preferably, the vapor feed stream in line 108 is at a sufficient temperature to remain in the vapor phase. The temperature of the vapor feed stream in line 108 is preferably from 50° C. to 200° C., e.g., from 90° C. to 175° C. or from 100° C. to 170° C. In one embodiment, vapor feed stream 108 may be further preheated prior to being fed to reactor 104. The process may control the vapor-phase esterification reaction temperature by super-heating the vaporized feed in line 108 using a heat exchanger that is used to control the reactor inlet temperature.

Any feed that is not vaporized is removed from vaporizer 107 and may be recycled or discarded. In one embodiment, there may be a relatively small blowdown stream 109 that comprises heavy compounds that may be withdrawn from vaporizer 107. Blowdown stream 109 may be reboiled as necessary. The mass flow ratio of the vapor feed stream 108 to blowdown stream 109 may be greater than 5:1, e.g., greater than 50:1, or greater than 500:1. When ethanol from hydrogenolysis zone 102 is recycled to esterification zone 101, the ethanol may contain heavy compounds such as higher alcohols and/or higher acetates. These heavy compounds may buildup in the blowdown stream 109.

Although vaporizer 107 preferably comprises little or no acidic catalyst, due to the vaporization conditions, some acetic acid and ethanol may be esterified. Thus, vaporizer 107 may be a non-catalyzed reactor that produces ethyl acetate. Thus, vapor feed stream in line 108 in addition to containing acetic acid and ethanol, may also comprise minor amounts of ethyl acetate, e.g., in an amount of less than 15 wt. % based on the total weight of the vapor feed stream in line 108, e.g., less than 10 wt. % or less than 5 wt. %. In addition to the minor amounts of ethyl acetate, in one embodiment, vapor feed stream in line 108 may comprise a weight majority of ethanol, e.g., at least 40 wt. %, at least 50 wt. % or at least 60 wt. %.

In one optional embodiment, there may be a liquid reactor (not shown) prior to vaporizer 107. The liquid reactor may contain a suitable acidic catalyst. Acetic acid feed stream in line 105 and ethanol feed stream in line 106 may be fed to the liquid reactor which produces an intermediate mixture that is vaporized. The additional feeds of acetic acid and ethanol may be fed with the intermediate mixture to vaporizer 107.

Vapor feed stream in line 108 is shown as being directed to the side of reactor 104, but in further embodiments, line 108 may be directed to the top, upper portion, or bottom of reactor 104. Reactor 104 contains the catalyst that is used in the esterification of acetic acid and ethanol. In one embodiment, one or more guard beds (not shown) may be used upstream of the reactor, optionally upstream of the vaporizer 107, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

The vapor-phase esterification reaction temperature is effected by the steady state composition and pressure, and typically may range from 50° C. to 200° C., e.g., from 80° C. to 190° C., from 125° C. to 175° C. In one embodiment, the esterification process may be operated at atmospheric pressure but it is preferably operated at super-atmospheric pressure, e.g., from 105 to 700 kPa, from 110 to 350 kPa or from 120 to 300 kPa. It is preferred to operate the esterification process at lower pressures of less than 700 kPa when no hydrogen is fed to the esterification reactor. When a hydrogen feed 110 is introduced to vaporizer 107, as shown in FIG. 2, it is preferred to operate esterification reactor at a substantially similar or greater pressure than hydrogenolysis zone 102. In one embodiment, when hydrogen is present, the esterification reactor may operate at a pressure from 700 kPa to 2,900 kPa, or more preferably from 1,500 kPa to 2,850 kPa, or from 2,000 kPa to 2,800 kPa. Operating an esterification reactor above 3,000 kPa may have an adverse impact on the esterification reaction and reduce the productivity of the esterification reactor.

During the esterification process, a reactor effluent is withdrawn in vapor phase, preferably continuously, from reactor 104 via line 103. The composition of the vapor reactor effluent may vary slightly provided that when the vapor reactor effluent is condensed the components do not phase into an aqueous and organic portion. As shown in Table 1, the esterification product, without hydrogen, may comprise the following exemplary compositions.

TABLE 1

SINGLE PHASE ESTERIFICATION PRODUCT

| Component | Conc. (wt. %) | Conc. (wt. %) | Conc. (wt. %) |
|---|---|---|---|
| Ethyl Acetate | 20 to 60 | 25 to 55 | 25 to 40 |
| Ethanol | 20 to 70 | 30 to 65 | 40 to 60 |
| Water | 1 to 30 | 2 to 25 | 5 to 20 |
| Acetic Acid | 0 to 15 | 0.01 to 10 | 0.1 to 1 |

The trace impurities, such as diethyl ether, acetaldehyde, diethyl acetal, n-butyl acetate, 2-butyl acetate, iso-propyl acetate, n-butanol, 2-butanol, and/or iso-propanol, may be present in small amounts, if at all.

When hydrogen is fed, as shown in FIG. 2, reactor effluent 111 may comprise hydrogen in addition to the components identified in Table 1. Reactor effluent 111 may comprise from 70 mol. % to 95 mol. % hydrogen. The concentration of hydrogen may be up to 30 wt. %, e.g., up to 25 wt. % or up to 20 wt. %.

Hydrogenolysis Reaction

As stated above and shown in FIG. 1, reactor effluent 103 is directly fed to hydrogenolysis zone 102 without any work-up or purification. This reduces the capital and energy requirements to obtain the ester feed to the hydrogenolysis zone 102. Reactor effluent 103 may be condensed and fed to hydrogenolysis zone 102 as a liquid stream or a partial liquid-gas stream. As shown in FIG. 1, reactor effluent 103 and hydrogen via feed line 120 are separately introduced into a vaporizer 122 to create a vapor feed stream in line 124 that is directed to hydrogenolysis reactor 126. In one embodiment, the molar ratio of water to hydrogen in feed line 120 is from 1:5 to 1:25, e.g., from 1:10 to 1:20. In one embodiment, reactor effluent 103 and hydrogen in line 120 may be combined and jointly fed to vaporizer 122. A vapor feed stream in line 124 is withdrawn may be preheated by passing through a heat exchanger. The temperature of the vapor feed stream in line 124 after passing through the heat exchanger is preferably from 100° C. to 350° C., e.g., from 200° C. to 325° C. or from 250° C. to 300° C. Vaporizer 122 preferably operates at a pressure from 700 to 8,500 kPa, e.g., from 1,500 to 7,000 kPa, or from 2,000 to 6,500 kPa. Any feed that is not vaporized is removed from vaporizer 122 as a blowdown stream 128. Blowdown stream 128 may be discarded from the hydrogenolysis zone 102.

Although vapor feed stream in line 124 is shown as being directed to the upper portion of hydrogenolysis reactor 126, line 124 may be directed to the side, top, or bottom of hydrogenolysis reactor 126.

Hydrogen fed to hydrogenolysis reactor 126 may be obtained from syngas. In addition, hydrogen may also originate from a variety of other chemical processes, including ethylene crackers, styrene manufacturing, and catalytic reforming. Commercial processes for purposeful generation of hydrogen include autothermal reforming, steam reforming and partial oxidation of feedstocks such as natural gas, coal, coke, deasphalter bottoms, refinery residues and biomass. Hydrogen may also be produced by electrolysis of water. In one embodiment, the hydrogen is substantially pure and contains less than 10 mol. % carbon monoxide and/or carbon dioxide, e.g., less than 5 mol. % or less than 2 mol. %.

In one embodiment, the molar ratio of hydrogen to ethyl acetate that is introduced into hydrogenolysis reactor 126 is greater than 2:1, e.g. greater than 4:1, or greater than 12:1. In terms of ranges the molar ratio may be from 2:1 to 100:1, e.g., 4:1 to 50:1, or from 12:1 to 20:1. Without being bound by theory, higher molar ratios of hydrogen to ethyl acetate, preferably from 8:1 to 20:1, are believed to result in high conversion and/or selectivity to ethanol.

Hydrogenolysis reactor 126 may comprise any suitable type of reactor, such as a fixed bed reactor or a fluidized bed reactor. Hydrogenolysis reactions are exothermic and in many embodiments, an adiabatic reactor may be used for the hydrogenolysis reactor. Adiabatic reactors have little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used.

In preferred embodiments, a catalyst is employed in a fixed bed reactor, e.g., in the shape of a pipe or tube, where the reactants, typically in vapor form, are passed over or through the catalyst. Other reactors, such as fluid or ebullient bed reactors, can be employed. In some instances, a hydrogenolysis catalyst may be used in conjunction with an inert material to regulate the pressure drop of the reactant stream through the catalyst bed and the contact time of the reactant compounds with the catalyst particles.

The hydrogenolysis process may be operated in a vapor phase, or a mixed vapor/liquid phase regime. The mixed vapor/liquid phase regime is where the reactant mixture in line 124, at the reactor conditions, is below the dew point temperature. The hydrogenolysis reaction may change from a mixed vapor/liquid phase to a fully vapor phase reaction, as the reaction proceeds down the reactor. The mixed phase hydrogenolysis may also be conducted in other types of reactors, or within a combination of different reactors, for example in a slurry or stirred tank reactor with, or without, external circulation and optionally operated as a cascade or stirred tank, a loop reactor or a Sulzer mixer-reactor. The hydrogenolysis process may be conducted in batch, semi-continuous, or continuous mode. For industrial purposes, continuous mode of operation is the most efficient.

In some embodiments, the hydrogenolysis reactor may comprise other types of reactors, such as fluidized bed, spinning basket and buss loop, or heat exchanger reactors. A mixed vapor/liquid phase hydrogenolysis reaction can be conducted with co-flow or counterflow of the vapor, e.g., hydrogen, to the liquid, i.e. ester feed stream, in a bubble reactor. Trickle bed reactors may also be used.

In one embodiment, a heterogeneous catalyst is used in hydrogenolysis reactor 126. The catalyst may be a copper-based catalyst. Copper-based catalyst may comprise copper chromite, copper and zinc, and/or copper-zinc-oxide. Other copper-based catalyst may include an $MgO$—$SiO_2$ support that is impregnated with copper. Mixed copper oxide based catalyst may include copper and a second metal selected from zinc, zirconium, manganese, and/or oxides thereof. In some embodiments, aluminum oxide may also be present in the catalyst. The presence of aluminum oxide is believed to increase the heavy alcohol, and/or ketone concentrations during the reduction of ethyl acetate due to the presence of acidic sites. In those embodiments, the catalyst may comprise a basic component, such as magnesium or calcium, to reduce the acidic sites or the aluminum oxide concentration may be very low, e.g., less than 0.1 wt. %. In some embodiments, the catalyst may be substantially free of aluminum oxide.

A suitable copper-based catalyst may comprises from 30 to 70 wt. % copper oxide, 15 to 45 wt. % zinc oxide, and/or 0.1 to 20 wt. % aluminum oxide. More preferably, a copper-based catalyst may comprises from 55 to 65 wt. % copper oxide, 25 to 35 wt. % zinc oxide, and/or 5 to 15 wt. % aluminum oxide. Preferably, the copper-based catalyst is supported on zinc oxide and preferably comprises from 20 to 40 wt. % of copper, in terms of the metal content.

In other embodiments, the catalyst employed in hydrogenolysis reactor 126 may be a Group VIII-based catalyst. Group VIII-based catalyst may comprise a Group VIII metal selected from the group consisting of iron, ruthenium, osmium, cobalt, rhodium, iridium, nickel, palladium, and platinum. In addition, there may be one or more secondary promoter metals selected from the group consisting of zinc, cobalt, tin, germanium, lead, rhenium, tungsten, molybdenum. Group VIII-based catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. In addition, the Group VIII-based catalyst may be supported on any suitable support, such as silica, silica-alumina, calcium metasiciliate, carbon, titania, clays, aluminas, zinc oxide, zirconia, and mixed metal oxides. For example, palladium based catalysts may be supported on carbon.

The reduction of ethyl acetate to produce ethanol, e.g., in the hydrogenolysis reactor 126, is typically conducted at elevated temperatures from 125° C. to 350° C., e.g., from 180° C. to 345° C., from 225° C. to 310° C., or from 290° C. to 305° C. Reaction temperatures greater than 240° C., or greater than 260° C., may increase conversion of ethyl acetate. Although not bound by theory, it is believed that reduced temperatures in the hydrogenolysis reactor of less than 275° C. may suppress the formation of heavy impurities such as alcohols and/or ketones. The pressure in the hydrogenolysis reactor may operate under high pressure of greater than 1000 kPa, e.g., greater than 3,000 kPa or greater than 5,000 kPa. In terms of ranges the pressure in the hydrogenolysis reaction may be from 700 to 8,500 kPa, e.g., from 1,500 to 7,000 kPa, or from 2,000 to 6,500 kPa. A pressure greater than 2,500 kPa may be more favorable for improving ethanol productivity and/or selectivity. The reactants may be fed to hydrogenolysis reactor at a gas hourly space velocity may range from 50 to 20,000 hr$^{-1}$, e.g., from 1000 to 10,000 hr$^{-1}$, or from 2000 to 7,000 hr$^{-1}$.

In some embodiments as shown in FIG. 2, when hydrogen is introduced to and passes through esterification reactor, the pressure of hydrogenolysis reactor may be from 700 to 2,900 kPa. The operating pressure of hydrogenolysis reactor may be substantially equal to or less than the pressure of the esterification reactor.

In particular, the reaction of ethyl acetate may achieve favorable conversion of ethyl acetate and favorable selectivity and productivity to ethanol. For purposes of the present invention, the term "conversion" refers to the amount of ethyl acetate in the feed that is converted to a compound other than ethyl acetate. Conversion is expressed as a mole percentage based on ethyl acetate in the feed. The conversion may be at least 50%, e.g., at least 70%, at least 90%. In terms of ranges, the conversion of ethyl acetate may range from 50 to 98%, e.g., from 60 to 95% or from 70 to 90%. Although catalysts and reaction conditions that have high conversions may be possible, such as greater than 90% or greater than 95%, in some embodiments a low conversion may be acceptable at high selectivity for ethanol. Compensating for low conversion by appropriate recycle streams or use of larger reactors may be easier than compensating for poor selectivity to ethanol.

Selectivity is expressed as a mole percent based on converted ethyl acetate. It should be understood that each compound converted from ethyl acetate has an independent selectivity and that selectivity is independent from conversion. For example, if 90 mole % of the converted ethyl acetate is converted to ethanol, we refer to the ethanol selectivity as 90%. The selectivity to ethanol is preferably at least 80%, e.g., at least 90% or at least 95%.

The term "productivity," as used herein, refers to the grams of a specified product, e.g., ethanol, formed during the hydrogenolysis, based on the kilograms of catalyst used per hour. A productivity of at least 100 grams of ethanol per kilogram of catalyst per hour, e.g., at least 500 grams of ethanol per kilogram of catalyst per hour or at least 1,000 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

A crude reaction product is preferably withdrawn continuously from hydrogenolysis reactor 126 via line 130. Any water in ester feed stream may pass through the hydrogenolysis reactor and be present in a similar amount in the crude reaction product. The composition of the crude reaction product may vary depending on the single phase reactor effluent, conversion, and selectivity. Exemplary crude reaction products, excluding hydrogen and other gases such as methane, ethane, carbon monoxide and/or carbon dioxide, are shown in Table 2 below.

TABLE 2

| CRUDE REACTION PRODUCT | | | |
|---|---|---|---|
| Component | Conc. (wt. %) | Conc. (wt. %) | Conc. (wt. %) |
| Ethanol | 70 to 97 | 75 to 95 | 80 to 90 |
| Ethyl Acetate | 1 to 15 | 1 to 10 | 1 to 8 |
| Water | 1 to 15 | 1 to 10 | 1 to 8 |
| Acetic Acid | 0 to 5 | 0.001 to 1 | 0.01 to 0.5 |

Organic compounds that have a larger molecular weight than ethanol, such as n-butyl acetate, sec-butyl acetate, ethyl butyrate, isopropyl acetate, 2-methyl-1-propanol, etc., may be present in minor amounts. Other acetates, aldehydes, and/or ketones may also be encompassed by such organic compounds. In some embodiments, the crude reaction product may comprise carbon gases, which includes refer to any carbon containing compound that is a gas at standard temperature and pressure, such as carbon monoxide, carbon dioxide, methane, ethane, etc. In one embodiment, the hydrogenolysis reaction is controlled to maintain low impurity concentrations of acetone, n-butanol, and 2-butanol.

The crude reaction product in line 130 may be condensed and fed to a separator 132, which, in turn, provides a vapor stream 134 and a liquid stream 136. In some embodiments, separator 132 may comprise a flasher or a knockout pot. Although one separator 132 is shown, there may be multiple separators in some embodiments of the present invention. The separator 132 may operate at a temperature of from 20° C. to 250° C., e.g., from 30° C. to 225° C. or from 60° C. to 200° C. The pressure of separator may range from 700 to 8,500 kPa, e.g., from 1,500 to 7,000 kPa, or from 2,000 to 6,500 kPa. When dual flashers are used, it is preferred to use a high pressure flasher followed by a low pressure flasher.

Vapor stream 134 exiting separator 132 may comprise hydrogen, carbon monoxide, carbon dioxide, and hydrocarbons, and may be purged and/or returned to hydrogenolysis reactor 126. In some embodiments, the returned vapor stream 134 may be compressed before being combined with hydrogen feed 120.

In one embodiment, as shown in FIG. 2, vapor stream 134 may pass through compressor 138 and is returned to hydrogen feed in line 110 to esterification zone 101. This allows esterification zone 101 to operate at a higher pressure. In one embodiment, esterification zone 101 may operate at a pressure that is similar to hydrogenolysis zone 102, e.g. from 700 to 8,500 kPa. When operating at higher pressure, reactor effluent in line 111 does not need to be vaporized prior to hydrogenolysis reactor 126. Although it may be necessary to pre-heat, reactor effluent 111 contains the reactants, namely hydrogen and ethyl acetate, to be reacted in hydrogenolysis reactor 126.

In FIGS. 1 and 2, liquid stream 136 is further separated to recover ethanol. Liquid stream 136 is fed to a lower portion of a distillation column 140. Although one column in shown, in other embodiments there may be a plurality of column to recover ethanol. From the perspective of capital and energy requirements it is preferred to reduce the number of columns. Column 140 produces an ethanol sidestream in line 142, a distillate in line 144 and a residue in line 146. Preferably ethanol sidestream 142 is the largest stream withdrawn from column 140 and is withdrawn at a point above the feed point of liquid stream 136. In one embodiment the relative flow ratios of sidestream to residue is greater than 50:1, e.g., greater than 100:1 or greater than 150:1.

Ethanol sidestream 142 preferably comprises at least 90% ethanol, e.g., at least 92% ethanol and at least 93% ethanol. Depending on the amount of water fed to hydrogenolysis reactor 126, the water concentration in ethanol sidestream 142 may be less than 10 wt. %, e.g., less than 8 wt. % or less than 7 wt. %. There may be higher amounts of water due to the single phase esterification product. In addition, the amount of other impurities, in particular diethyl acetal and 2-butanol, are preferably less than 0.05 wt. %, e.g., less than 0.03 wt. % or less than 0.01 wt. %. The distillate in line 144 preferably comprises a weight majority of the diethyl acetal fed to column 140. In addition, other light components, such as acetaldehyde and/or ethyl acetate may also concentrate in the distillate. The residue in line 146 preferably comprises a weight majority of the 2-butanol fed to column 140. Heavier alcohols may also concentrate in the residue in line 146.

Column 140 may be a tray column or packed column. In one embodiment, column 140 is a tray column having from 10 to 100 trays, e.g., from 20 to 80 trays or from 30 to 70 trays. Column 140 operates at a pressure ranging from 1 kPa to 510 kPa, e.g., from 10 kPa to 450 kPa or from 50 kPa to 350 kPa. Although the temperature of column 140 may vary, the temperature of the residue exiting in line 146 preferably is from 70° C. to 105° C., e.g., from 70° C. to 100° C. or from 75° C. to 95° C. The temperature of the distillate exiting in line 144 preferably is from 50° C. to 90° C., e.g., from 55° C. to 85° C. or from 65° C. to 80° C. Ethanol sidestream 142 is preferably withdrawn at the boiling point of ethanol, about 78° C. at atmospheric pressure.

The ethanol product may contain small concentrations of water. For some ethanol applications, in particular for fuel applications, it may be desirable to further reduce the water concentration for producing anhydrous ethanol. As shown, ethanol sidestream 142 is fed to a water separation unit 150. Water separation unit 150 may include an adsorption unit, one or more membranes, molecular sieves, extractive distillation units, or a combination thereof. Ethanol sidestream 142 may be withdrawn as a vapor or liquid stream, but it may be more suitable to use a vapor stream. Suitable adsorption units include pressure swing adsorption (PSA) units and thermal swing adsorption (TSA) units. A PSA unit 150 may be employed to remove water from the sidestream 142. PSA unit 150 is operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. The resulting dried ethanol product stream 152 preferably has a water concentration that is less than 1 wt. %, e.g., less than 0.5 wt. % or less than 0.1 wt. %. The water stream 154 may be purged.

A return portion of the ethanol in line 156 may be taken after water is removed. In one embodiment, less than half of the ethanol in line 152 is returned via line 156. In other embodiments, the ethanol returned to esterification zone may be separated prior to the water separation unit to increase the capacity of the water separation unit. This allows an impure ethanol recycle and does not require additional capital to purify the ethanol prior to returning the ethanol to esterification zone.

In some embodiments, a portion of the residue may be dehydrated to form aliphatic alkenes. In one embodiment, the 2-butanol in the residue may be dehydrated to 2-butene. In another embodiment, the 2-butanol in the residue stream may be recovered in a separate system.

In one embodiment, instead of purging the residue in line 146, a portion thereof may be fed to vaporizer 107. Heavy ends compounds may be removed in the blowdown stream 109.

Preferably column 140 operates to maintain a low concentration of ethyl acetate in the residue in line 146, e.g., less than 1 wt. %, less than 0.1 wt. % or less than 0.01 wt. %. The distillate in line 144 preferably is refluxed at a ratio sufficient to maintain low concentrations of ethyl acetate in the residue and minimize ethanol concentrations in the distillate, and reflux ratio may vary from 30:1 to 1:30, e.g., from 10:1 to 1:10 or from 5:1 to 1:5. Distillate in line 144 may comprise ethyl acetate and/or ethanol. In one embodiment, distillate in line 144 may be returned, directly or indirectly, to hydrogenolysis reactor 126. When hydrogenolysis reactor 126 operates at a lower ethyl acetate conversion, e.g. less than 90% conversion, less than 85% conversion or less than 70% conversion, it may be possible to recycle ethyl acetate back to hydrogenolysis reactor 126. Distillate in line 144 is condensed and combined with reactor effluent in line 103 before or in vaporizer 122. When combined before vaporizer the additional ethyl acetate in line 144 should be in a portion that does not cause reactor effluent 103 to phase. In FIG. 2, distillate in line 144 may be fed directly vaporizer 107, hydrogenolysis reactor 126 or combined with reactor effluent in line 103. In some embodiment, distillate in line 144 may be withdrawn as a vapor or separately vaporized as needed prior to being combined with reactor effluent in line 103. Advantageously, this embodiment may avoid recycling ethanol through hydrogenolysis reactor 126 that may lead to capacity restraints and additional capital costs. When returning distillate in line 144 to hydrogenolysis reactor 126, it is preferred to operate column 140 with a design and under conditions that minimize the ethanol to ethyl acetate ratio, e.g., distillation trays and/or reflux ratio.

Optionally, distillate in line 144 may be returned, directly or indirectly, to esterification zone 101 when there is a larger ethanol concentration. This also allows column 140 to operate under less stringent conditions, e.g., with a lower reflux ratio. Distillate in line 144 may be combined with either the acetic acid feed stream in line 105 or ethanol feed stream in line 106. When distillate in line 144 is returned to esterification reactor 103, it may be possible to return a relatively larger amount of ethanol. In addition, when an appreciable amount of alcohols having at least 4 carbons, such as n-butanol and/or 2-butanol, are produced through side reactions in the hydrogenolysis reactor 126, it is preferred not to return these higher alcohols to the esterification step as the higher alcohols may react with acetic acid leading to a buildup of higher acetates in the process.

The columns shown in the figures may comprise any distillation column capable of performing the desired separation and/or purification. For example, unless described otherwise, the columns may be tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

For purposes of the present invention, exemplary ethanol compositional ranges are provided below in Table 3. Depending on the application of the ethanol, one or more of the other organic impurities listed in Table 3 may be present.

TABLE 3

FINISHED ETHANOL COMPOSITIONS

| Component | Conc. (wt. %) | Conc. (wt. %) | Conc. (wt. %) |
|---|---|---|---|
| Ethanol | 75 to 99.9 | 88 to 99.5 | 90 to 96 |
| Water | <12 | 0.01 to 7.5 | 0.5 to 5 |
| Acetic Acid | <0.1 | <0.01 | <0.005 |
| Ethyl Acetate | <0.1 | <0.01 | <0.005 |
| Isopropanol | <0.5 | <0.1 | <0.05 |
| Diethyl Acetal | <0.5 | <0.1 | <0.05 |
| n-butanol | <0.5 | <0.1 | <0.05 |
| 2-butanol | <2 | <0.5 | <0.1 |
| Acetone | <0.5 | <0.1 | <0.05 |

In one embodiment, the recovered ethanol may have a composition that is from 92 wt. % to 97 wt. % ethanol, 3 wt. % to 8 wt. % water, 0.01 wt. % to 0.2 wt. % 2-butanol, and 0.02 wt. % to 0.08 wt. % isopropanol. The amount of 2-butanol may be greater than isopropanol. Preferably, other than 2-butanol and isopropanol, the recovered ethanol comprises less than 1 wt. % of one or more organic impurities selected from the group consisting of acetaldehyde, acetic acid, diethyl acetal, and ethyl acetate. The 2-butanol concentration in the ethanol sidestream may be reduced to an amount that is less than 0.01 wt. % when using a finishing column.

Ethanol produced by the embodiments of the present invention may be used in a variety of applications including fuels, solvents, chemical feedstocks, pharmaceutical products, cleansers, sanitizers, hydrogen transport or consumption. In fuel applications, ethanol may be blended with gasoline for motor vehicles such as automobiles, boats and small piston engine aircraft. In non-fuel applications, ethanol may be used as a solvent for toiletry and cosmetic preparations, detergents, disinfectants, coatings, inks, and pharmaceuticals. Ethanol may also be used as a processing solvent in manufacturing processes for medicinal products, food preparations, dyes, photochemicals and latex processing.

Ethanol may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, ethanol may be esterified with acetic acid. In another application, ethanol may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, examples are provided below. It should be understood that these examples are for illustrative purposes only and are not to be construed as limiting the invention in any manner.

EXAMPLES

The following examples were prepared with ASPEN Plus 7.1 simulation software to test various feed composition and separation systems.

Example 1

Acetic acid and ethanol are fed at a molar ratio of 1:4 to a vaporizer to produce a vapor stream having a temperature of 226° C. The vapor stream is fed to an esterification reactor having a suitable acidic catalyst to produce an effluent comprising 56.7 wt. % ethanol, 35.7 wt. % ethyl acetate, 7.3 wt. % water and 0.2 wt. % acetic acid. The effluent is condensed and fed to a vaporizer along with a separate hydrogen stream. The molar ratio of hydrogen to ethyl acetate is 20:1. The hydrogenolysis reaction is conducted at a temperature of 210° C. and a pressure of 4240 kPa. The crude ethanol product withdrawn from the hydrogenolysis reaction comprises 76.5 wt. % ethanol, 6.2 wt. % ethyl acetate, 5.8 wt. % water, and 0.002 wt. % acetic acid. The crude ethanol product is separated in a flasher and the hydrogen is returned to the vaporizer for the hydrogenolysis reactor. The liquid stream is fed to a distillation column. The distillation column separates the liquid portion of the crude ethanol product to yield an overhead comprising 41.2 wt. % ethyl acetate, 54.9 wt. % ethanol, and 3.8 wt. % water. The overhead is refluxed and returned to the vaporizer for the hydrogenolysis reactor. A sidedraw comprising 93.1 wt. % ethanol, and 6.8 wt. % water is taken from the distillation column as the ethanol product. Overall the process converts about 75% of the acetic acid to ethanol.

Example 2

Acetic acid and ethanol are fed at a molar ratio of 1:4 to a vaporizer along with hydrogen to produce a vapor stream that comprises 19.7 wt. % acetic acid, 61.5 wt. % ethanol, and 18.3 wt. % hydrogen. The vapor stream is fed to an esterification reactor having a suitable acidic catalyst, and operating at a pressure of 2859 kPa. The esterification reactor produces an effluent comprising 46.5 wt. % ethanol, 29.1 wt. % ethyl acetate, 5.9 wt. % water, 0.002 wt. % acetic acid, and 18.3 wt. % hydrogen. The effluent is fed to hydrogenolysis reactor. No separate hydrogen feeds are combined with the effluent prior the hydrogenolysis reactor and all the hydrogen fed to hydrogenolysis passes through the esterification reactor. The hydrogenolysis reaction is conducted at a temperature of 210° C. and a pressure of 2755 kPa. The crude ethanol product withdrawn from the hydrogenolysis reaction comprises 72.8 wt. % ethanol, 6.9 wt. % ethyl acetate, 5.6 wt. % water, and 0.002 wt. % acetic acid. The crude ethanol product is separated in a flasher and the hydrogen is returned to the vaporizer for the esterification reactor. The liquid stream is fed to a distillation column. The distillation column separates the liquid portion of the crude ethanol product to yield an overhead comprising 43 wt. % ethyl acetate, 53 wt. % ethanol, and 3.7 wt. % water. The overhead is refluxed and returned to the hydrogenolysis reactor. A sidedraw comprising 93.4 wt. % ethanol, and 6.5 wt. % water is taken from the distillation column as the ethanol product. Overall the process converts about 75% of the acetic acid to ethanol.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

The invention claimed is:

1. A method of producing ethanol comprising:
   esterifying acetic acid and ethanol in a first reaction zone to produce an effluent that comprises from 20 wt. % to 70 wt. % ethanol and is in a single phase, wherein the first reaction zone is operated in the vapor phase;
   adding hydrogen to the effluent to form a feed stream;
   reacting the feed stream in a second reaction zone under conditions to reduce ethyl acetate to ethanol to produce a crude reactor product; and
   recovering ethanol from the crude reactor product.

2. The method of claim 1, wherein the effluent comprises from 0 to 15 wt. % acetic acid.

3. The method of claim 1, wherein acetic acid and ethanol molar ratio in the first reaction zone is from 1:3 to 1:10.

4. The method of claim 1, wherein the feed stream comprises from 70 mol. % to 95mol. % hydrogen.

5. The method of claim 1, wherein the feed stream comprises water and hydrogen at a molar ration of 1:5 to 1:25.

6. The method of claim 1, wherein the crude reactor product comprises more ethanol than the effluent on a weight basis.

7. The method of claim 1, wherein the crude reactor product comprises:
   70 to 97 wt. % ethanol;
   1 to 15 wt. % ethyl acetate; and
   1 to 15 wt. % water.

8. The method of claim 1, further comprising:
   separating at least a portion of the crude reactor product in a distillation column and withdrawing a sidedraw comprising ethanol; and
   optionally dehydrating the sidedraw to obtain an ethanol product having less than 0.5 wt. % water.

9. The method of claim 1, wherein the second reaction zone operates at a pressure that is from 700 kPa to 8,500 kPa.

* * * * *